United States Patent [19]
Sava

[11] Patent Number: 5,931,777
[45] Date of Patent: Aug. 3, 1999

[54] TISSUE RETRACTOR AND METHOD FOR USE

[76] Inventor: Gerard A. Sava, 80 Mill River St., Stamford, Conn. 06902

[21] Appl. No.: 09/038,431

[22] Filed: Mar. 11, 1998

[51] Int. Cl.$^6$ .................................................. A61B 17/00
[52] U.S. Cl. ......................... 600/213; 600/210; 600/217; 600/219; 600/224; 600/213; 600/235
[58] Field of Search ..................................... 600/201, 210, 600/213, 214, 219, 224, 235, 217

[56] References Cited

U.S. PATENT DOCUMENTS

| | | |
|---|---|---|
| 569,839 | 10/1896 | Roeloffs . |
| 2,075,534 | 3/1937 | McCormack ............................ 600/219 |
| 2,238,563 | 4/1941 | Jacques ................................ 600/219 X |
| 2,541,516 | 2/1951 | Ivory et al. . |
| 2,751,903 | 6/1956 | Ivory et al. . |
| 3,038,467 | 6/1962 | Sovatkin ................................. 600/219 |
| 3,176,682 | 4/1965 | Wexler . |
| 3,278,207 | 10/1966 | Barish et al. ............................. 287/12 |
| 3,638,973 | 2/1972 | Poletti .................................... 285/184 |
| 3,858,578 | 1/1975 | Milo . |
| 5,271,384 | 12/1993 | McEwen et al. . |
| 5,529,571 | 6/1996 | Daniel .................................... 600/219 |
| 5,618,260 | 4/1997 | Caspar et al. ........................... 600/210 |
| 5,728,046 | 3/1998 | Mayer et al. ........................... 600/210 |

FOREIGN PATENT DOCUMENTS

| | | | |
|---|---|---|---|
| 963517 | 10/1982 | U.S.S.R. | ............................... 600/235 |

OTHER PUBLICATIONS

Surgical Enterprise Corporation Brochure "Shadow Line Soft Tissue Retractor Set", 1994.

*Primary Examiner*—Jeffrey A. Smith
*Attorney, Agent, or Firm*—St. Onge Steward Johnston & Reens LLC

[57] ABSTRACT

A tissue retractor with particular use in spinal surgery comprises a pair of pivotally linked arms, each with a blade mounted thereto by a ball and socket joint to allow the blades free movement relative to the arms. The blades have anchoring end to anchor to bone, which preferably are sharp piercing tips. The balls and the sockets are preferably detachable from each other. The retractor is operable by placing the blades in a wound opening; securing the anchoring ends to a portion of bone at positions a distance apart from each other to define a desired surgical field; and operating the retractor to cause the blades to separate and to retract tissues surrounding said wound opening by outward pivoting of the blades relative to the position of the anchoring ends. A supplemental retractor blade or blades may be provided by a linking armature for additional retraction generally perpendicularly to a retraction action provided by the main retractor blades.

29 Claims, 7 Drawing Sheets

TISSUE RETRACTOR AND METHOD FOR USE

FIELD OF THE INVENTION

The present invention relates to the field of surgical instruments, particularly, to retractors used by surgeons to displace tissue to allow access to a desired surgical field during a surgical procedure.

BACKGROUND OF THE INVENTION

In order to obtain access to the spine to provide surgical treatment of the spine and/or spinal cord, it is necessary to displace muscles and other tissues and anatomical structures. Thus for example, in performing a vertebral disc and cartilage removal, followed by interbody fusion of the spinal vertebrae, the surgical field is the anterior surface of the spine. In such case the approach to the anterior surface of the spine is made through the front of the patient's neck, between the trachea and the carotid artery. The conventional retractor used in this procedure comprises a pair of linked pivoting arms, each having a curved blade and a scissors grip, so that closing the scissors grips together causes the blades to move part. The blades of such retractors are used to separate the tissues to allow access to the surgical field. It has been found in actual practice that the conventional retractors will lose their grip of the retracted tissues, and/or will move from the surgical field of interest, often as much as 7–10 times during a procedure. Such slips and movements can be caused simply by the slippery nature of the human tissues, which tend to slide out of place even when initially correctly positioned; or can be caused by muscle contractions that may occur even in an anesthetized patient; or by movement of the patient; or by movement of the retractor by the surgical professionals seeking to improve vision of the surgical field of interest. Such slips and movements tend to lengthen the time required for the surgical procedure. It is to be appreciated that in most surgical procedures, time is of the essence, as a shorter procedure means less anesthesia, less extended period of trauma, and better and quicker rates of recovery from the surgery.

It would be desirable therefore, to provide a tissue retractor that provides for reduced likelihood of loss of the tissue retraction and of the surgical field, and therefore improved surgical outcomes.

SUMMARY OF THE INVENTION

It is an object of the invention to provide a tissue retractor that will tend to maintain its position in the patient's anatomy, once established by the surgeon.

It is an object of the invention to provide a tissue retractor that will tend to maintain its retraction of patient tissues without loss thereof, once established by the surgeon.

It is an object of the invention to provide a retractor that provides an improved working area above a surgical field of interest.

These objects, and other objects as disclosed in this application, are achieved as described below.

A preferred embodiment of a tissue retractor in accordance with the invention comprises a retractor with piercing blades capable of being fixed in bone, with swivel mountings between the blades and the retractor arms. Specifically, the retractor has a pair of arms, each having a finger grip section, and a pivotal connection between the pair of arms. A blade is mounted to each of the arms in a position remote from the finger grip sections and the pivotal connection. Swivel mountings, capable of free pivoting movement in at least one plane, and preferably multiple planes or directions, hold the blades to the arms.

Each swivel mounting preferably comprises a ball and socket joint, in which the ball is provided as part of the blade, and the socket is provided with the arm. In order to allow for thorough sterilization of the instrument, the ball is preferably detachable from the socket. In the preferred embodiment, the socket is split and axially movable in a receiving pocket in the arm of the tissue retractor. The split socket has petals which are sufficiently resilient to be moved apart to allow removal or insertion of the ball. When the split socket is nested in the receiving pocket of the retractor, the sidewalls of the receiving pocket hold the petals in place to engage and hold the ball in the socket. When the split socket is dropped out of the receiving pocket, the petals can be moved sufficiently to remove or insert the ball. Preferably, the split socket is axially movable in the receiving pocket by a finger operable sliding cam element fitted into a slot in an upper end of the socket.

In contrast to conventional retractors which are not fixed to the underlying bone, and which use a brute force approach to separate tissues to provide a surgical field, the present invention uses a different approach. In the present invention, the piercing tips are fixed to the underlying bone; when the arms are actuated, the blades pivot around the position of the piercing tips and spread apart the tissue from the pivot points. The result of this approach is to provide a surgical field of a selected area near the bone, but in which the incision opening above the surgical field is larger than surgical field. In contrast to conventional retractors where it is usually necessary to displace the entire thickness of the tissue to achieve a desired wound opening, in the present invention only the upper layers of tissue need be displaced to the full extent. Thus, a method of tissue retraction in accordance with the invention comprises placing the blades in a wound opening; securing the anchoring ends to a portion of the spine at positions a distance apart from each other to define a desired surgical field; operating the retractor to cause the blades to separate and to retract tissues surrounding the wound opening by outward pivoting of the blades relative to the position of the anchoring ends in their secured positions; and locking the retractor arms in a fixed position relative to each other.

Other objects, aspects and features of the present invention in addition to those mentioned above will be pointed out in detail or will be understood from the following detailed description provided in conjunction with the accompanying drawings.

BRIEF DESCRIPTION OF THE DRAWINGS

The foregoing aspects and other features of the invention are explained in the following description, taken in connection with the accompanying drawings, wherein.

DETAILED DESCRIPTION OF THE INVENTION

Referring now to FIGS. 1–17, wherein the same elements are identified by the same numbers, a tissue retractor 10 in accordance with the invention is shown. Tissue retractor 10 is especially adapted for spinal surgery where it is necessary to displace tissues anterior of the spine to allow access to the spinal vertebrae, however, it may be used in other applications where it is desired to displace tissues adjacent to bone matter in the body.

Figures 1, 3:
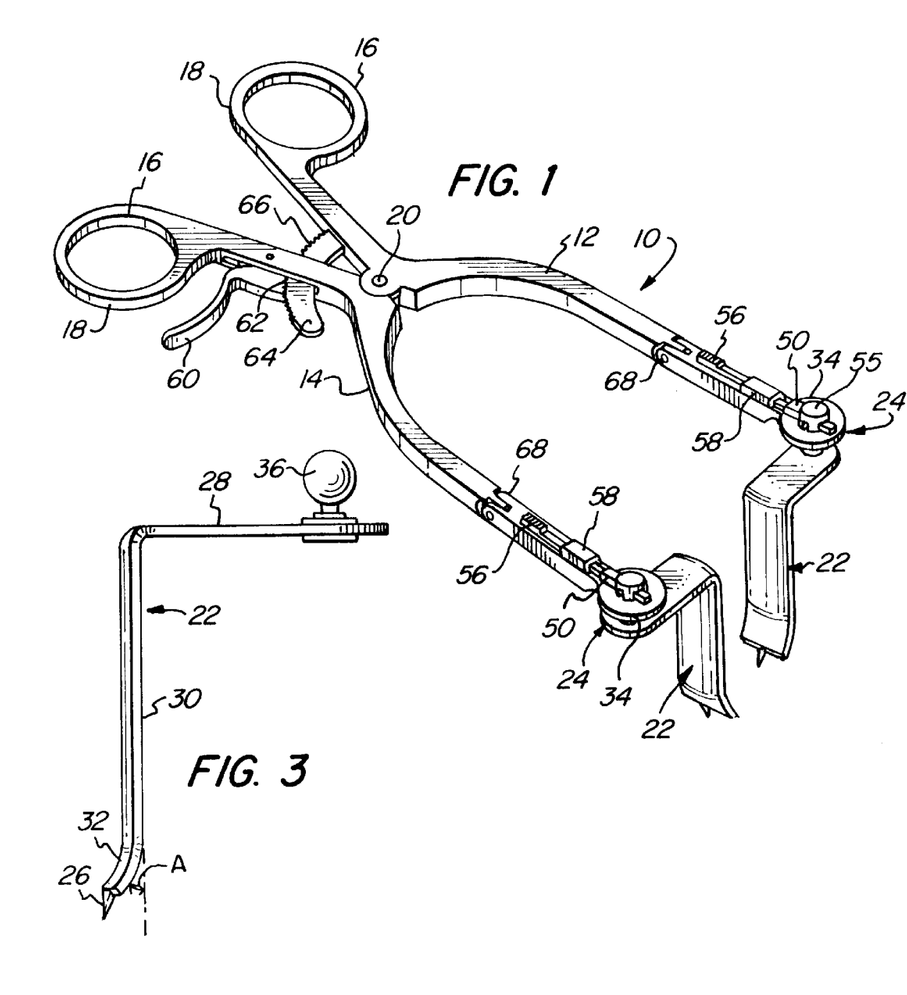
FIG. 1 is a top perspective view of an embodiment of a tissue retractor in accordance with the invention.
FIG. 3 is a side elevation view of the blade of FIG. 2.
Figures 2, 4:
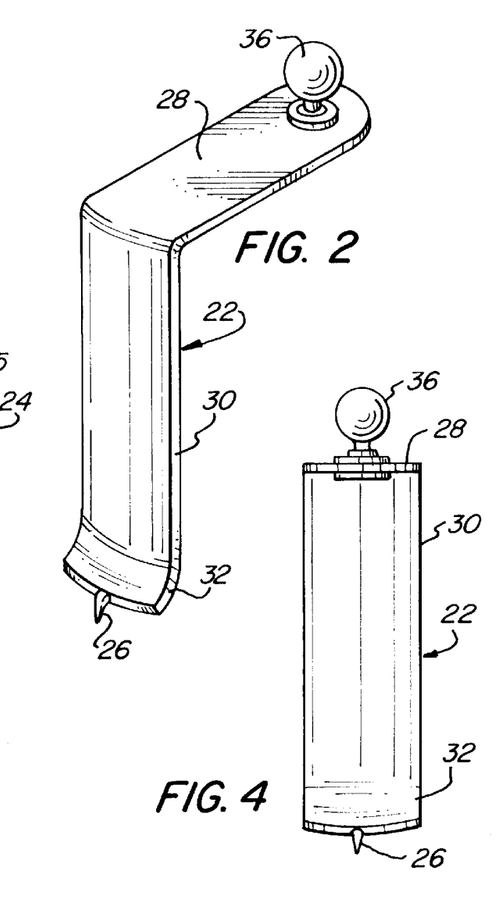
FIG. 2 is a top and front perspective view of a blade of the tissue retractor of FIG. 1.
FIG. 4 is a rear elevation view of the blade of FIG. 2.

Retractor 10 comprises a pair of arms 12 and 14. The arms 12 and 14 have finger grip loops 16 at proximal ends 18 thereof as are conventional in retractor design. A pivotal connection 20 connects the pair of arms 12 and 14 at mid-portion thereof. Pivotal connection 20 may comprise pivot pins on one arm 12 received in pivot pin holes on the other arm 14. A blade 22 is mounted to each of the arms 12 and 14 at distal ends 24 thereof. Operation of the retractor 10 by squeezing the finger grip loops 16 together causes distal ends 24 and the blades 22 mounted thereto to separate apart from each other, to thereby displace tissue as further described below.

Figure 7:
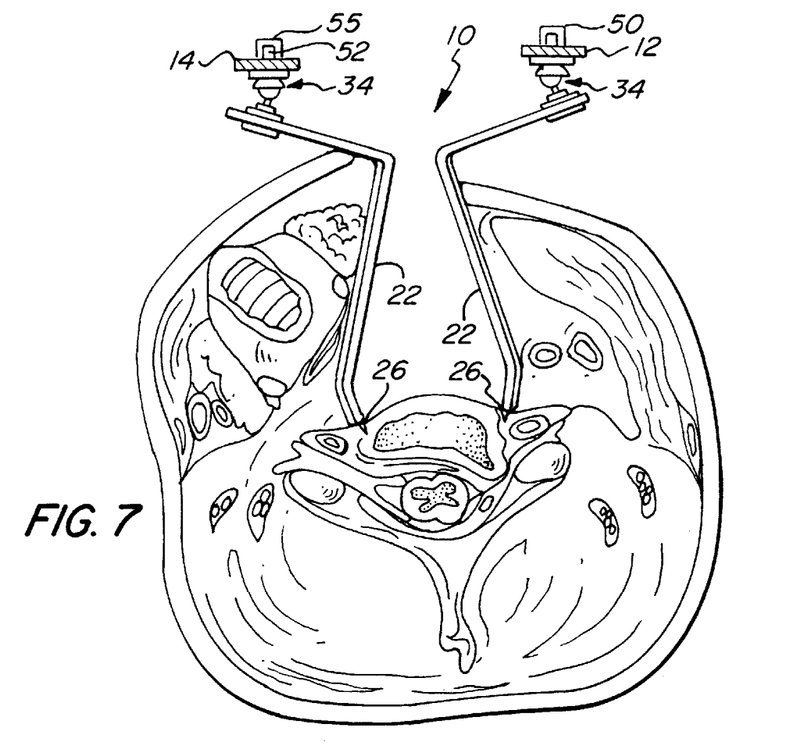
FIG. 7 is a view showing placement of blades of the tissue retractor of FIG. 1 in the anterior surface of the spine in preparation for tissue retraction.
Figure 8:
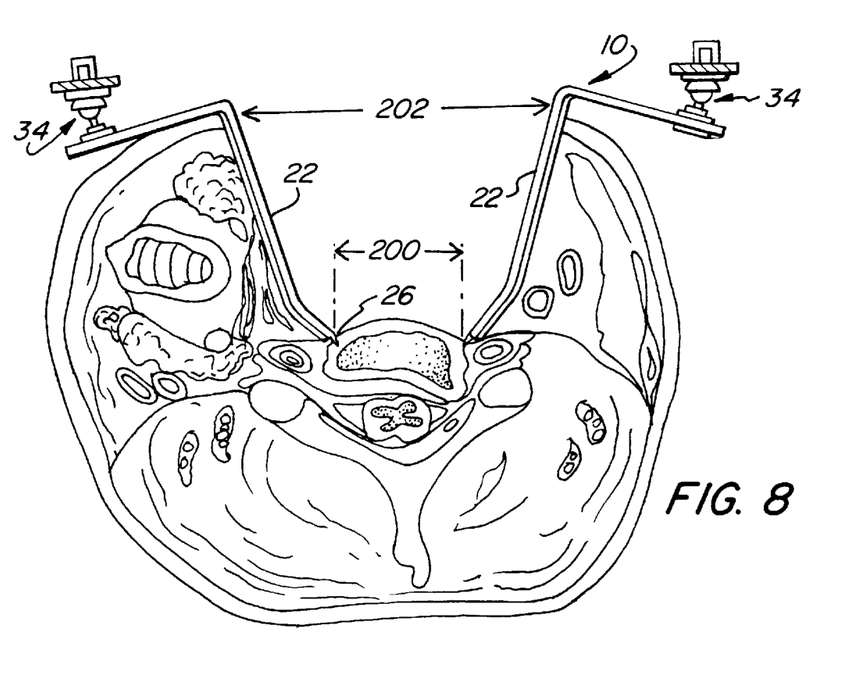
FIG. 8 is a view showing tissue retraction at the anterior surface of the spine using the tissue retractor of FIG. 1.
Figure 9:
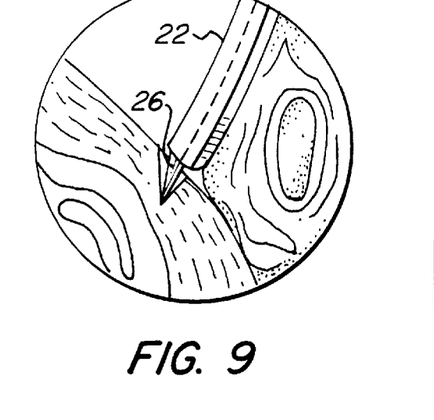
FIG. 9 is a detail view showing placement of the blade of the spinal tissue retractor of FIG. 1 to anchor the blade in position.
Figure 14:
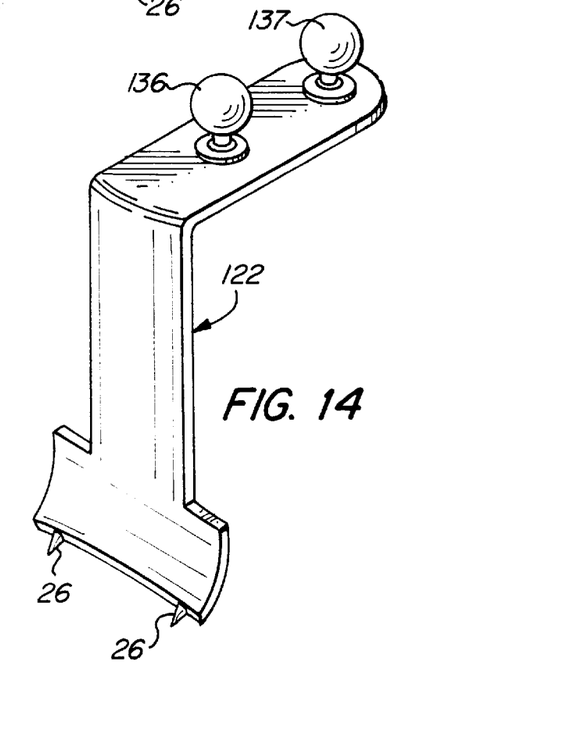
FIG. 14 is a perspective view of another embodiment of a blade of the spinal tissue retractor of FIG. 10.

The blades 22 are each provided with anchoring end capable of being anchored in bone matter. In the preferred embodiment, the anchoring end is a piercing tip 26, that can be anchored in human spinal vertebrae by application of sufficient force by tapping on the blades 22. As can be seen in FIGS. 1–4, blades 22 comprise four sections: a first section 28 extending inwardly from the distal ends 24 of the arms 12 and 14; a second section 30 extending downwardly from first section 28; a third section 32 extending inwardly and downwardly from second section 30; and the anchoring end represented by piercing tip 26. In general, second section 30 is perpendicular to the first section 28. The third section 32 is generally at an angle A to the axis of the second section 30. Angle A is typically in the range of 20° to 60°, and preferably at about a 30° to 45°, most preferably about a 30°. The angle A assists in the displacement of tissue by pivoting action provided by retractor 10 as shown in FIGS. 7–9 and as hereafter described. As shown in FIG. 14, the blade, shown at 122, may have more than one piercing tip 26, and/or the third section may have a different width than the first and second sections, to increase the size of the surgical field and/or the amount of tissue displaced, without increasing the size of components that might interfere with the surgeon's work.

Figure 16:
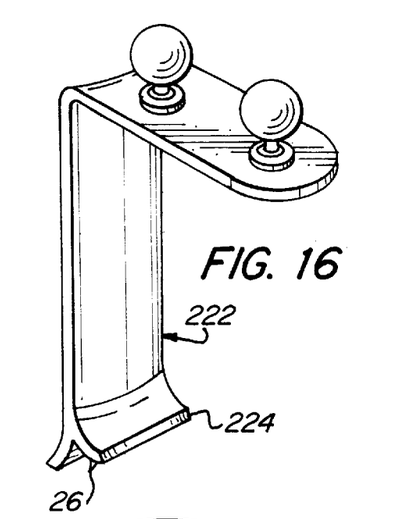
FIG. 16 is a perspective view of another embodiment of a blade of the spinal tissue retractor of FIG. 10.
Figure 17:
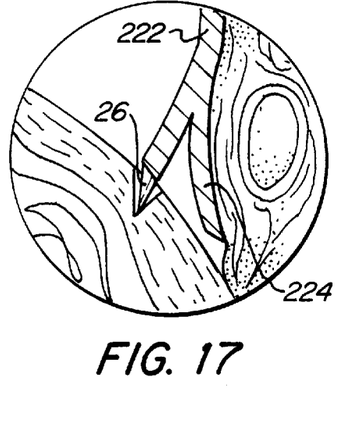
FIG. 17 is a detail view showing placement of the blade of the spinal tissue retractor of FIG. 16 to anchor the blade in position.

Another embodiment of a blade is shown in FIGS. 16–17. Blade 222 is identical to the blade shown in FIG. 13, but has an additional laterally projecting shelf 224. As can be seen in FIG. 17, shelf 224 pushes against the soft tissues when the retractor 10 is in use, and helps to prevent creeping of the soft tissues underneath the blade into the surgical field. This minimizes the chance of injury to the soft tissue that might occur if the soft tissues were allowed to spread out into the surgical field.

Blades 22 are mounted to the arms 12, 14 at their distal ends 24 with swivel mountings. The swivel mountings are capable of free pivoting movement in at least a single plane, and preferably, they are capable of pivoting movement in multiple directions. The swivel mountings preferably cannot be locked or fixed in any one position and are allowed to be always movable. In the preferred embodiment, the swivel mountings are ball and socket joints 34. As can be seen in FIGS. 2–6, preferably, the balls 36 of the ball and socket joints 34 are provided with the blades 22, and the sockets 38 of the ball and socket joints 34 are provided with the arms 12 and 14.

Figure 5:
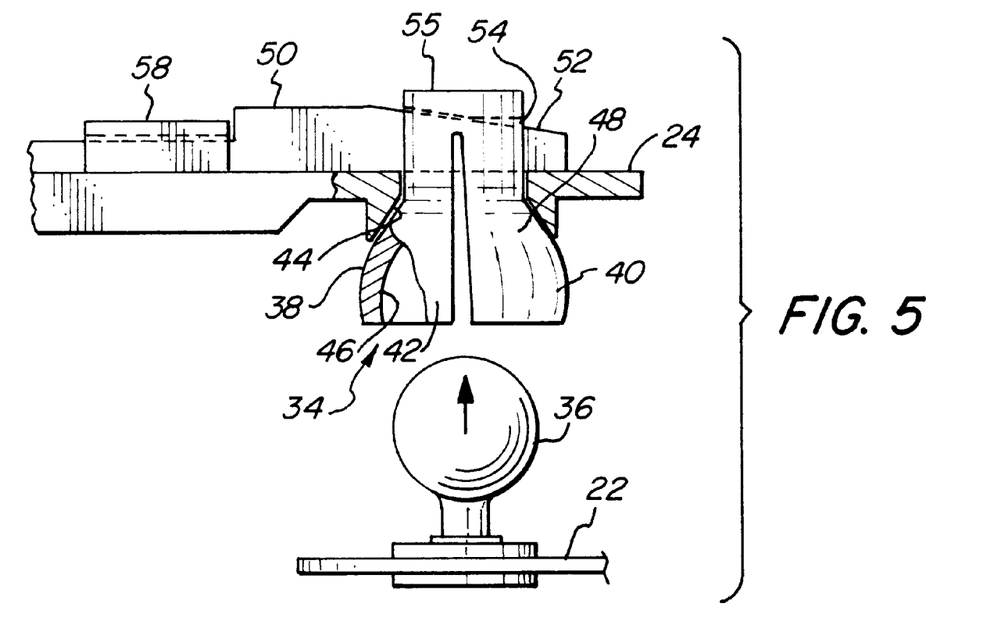
FIG. 5 is an exploded partial cross-sectional and side elevation view of a swivel joint between a blade and an arm of the tissue retractor of FIG. 1.
Figure 6:
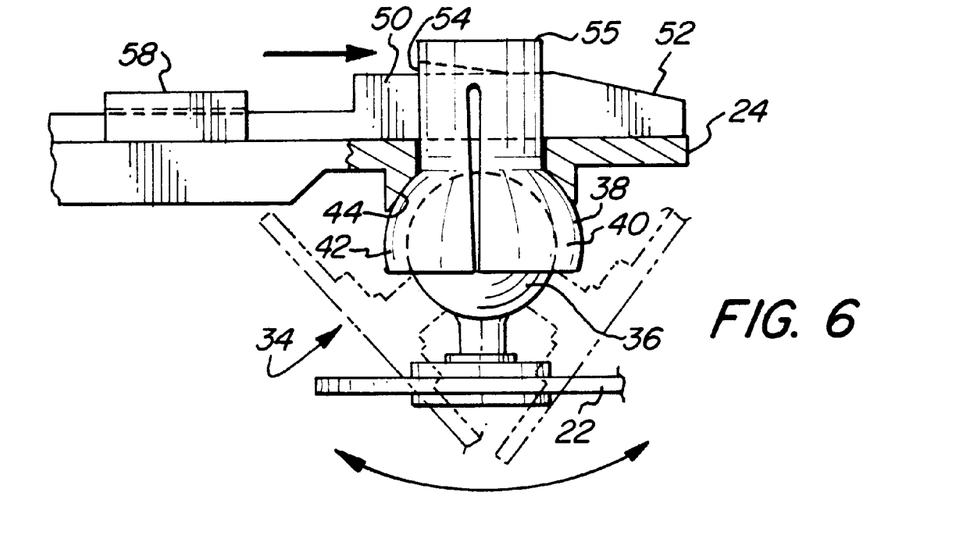
FIG. 6 is a partial cross-sectional and side elevation view of a swivel joint between a blade and an arm of the spinal tissue retractor of FIG. 1 showing a range of motion of the blade.

In order to allow for cleaning and sterilization, the balls 36 are preferably detachable from the sockets 38. In the preferred embodiment, as shown in FIGS. 5–6, the sockets 38 are split into petals such as portions 40 and 42, which have a limited degree of resilience so that the balls 36 can be removed from and inserted into the sockets 38. In order to securely hold the balls 36 in place when they are inserted in the sockets, a receiving pocket 44 is provided in each of the distal ends 24 of arms 12 and 14. Receiving pockets 44 surround the sockets 38 and receive the exterior walls of the socket 38. Preferably, the interior walls 46 and exterior walls 48 of the sockets 38 and their portions 40 and 42 are hemispherical, although, of course, the lower ends of the interior walls 46 should be spaced apart to provide a diameter which is sufficiently less than the maximum diameter of the balls 36, such that the balls 36 can be securely retained in the sockets 38. In such case, the receiving pockets 44 will have tapered walls (similar to a countersunk hole) or hemispherical walls, so that as the sockets 38 are placed in the receiving pockets 44, the walls of the receiving pockets 44 press against the exterior walls 48 of the sockets 38 to force the portions 40 and 42 together to trap and securely hold the balls 36 of the ball and socket joints 34.

A convenient and preferable way to effect the above described trapping of the balls 36 in the sockets 38 is by use of a sliding cam element 50. Sliding cam element 50 is a longitudinal bar with a cammed leading edge 52. Leading edge 52 fits into a slot 54 which is part of and provided at the upper end 55 of the socket 38. Cam element is provided with finger grips 56, so that it is finger operable. A cam element 50 is secured to each of the upper surfaces of the arms 12, 14 by a sleeve 58. The cam elements 50 slide longitudinally along the upper surfaces of the arms 12, 14 and through sleeve 58. The upper ends 55 of the sockets 38 extend upwardly through the arms 12, 14 through the receiving pockets 44, where the cam elements 50 may be manipulated to place them within the slots 54 to pull the sockets 38 upwardly, causing the walls of the receiving pockets 44 to bear against the exterior walls 48 of the sockets 38 to force the portions 40 and 42 together to trap and securely hold the balls 36 of the ball and socket joints 34. The cam elements 50 also serve to securely hold the sockets 38 to the arms 12, 14, as shown in FIG. 6.

Preferably, means for locking the arms in a fixed relationship are provided, and may comprise various ratchet mechanisms or screw tightened elements. In the preferred embodiment, as shown in FIG. 1, a simple locking ratchet mechanism wherein a thumb lever 60 with teeth 62 engages a curved ratchet bar 64 with mating teeth 66.

Preferably, the arms 12, 14 are both provided with a hinge 68 in portions thereof between their distal ends 24 and the pivotal connection 20 to allow for a broader range of operational angles of movement.

Figures 10, 15:
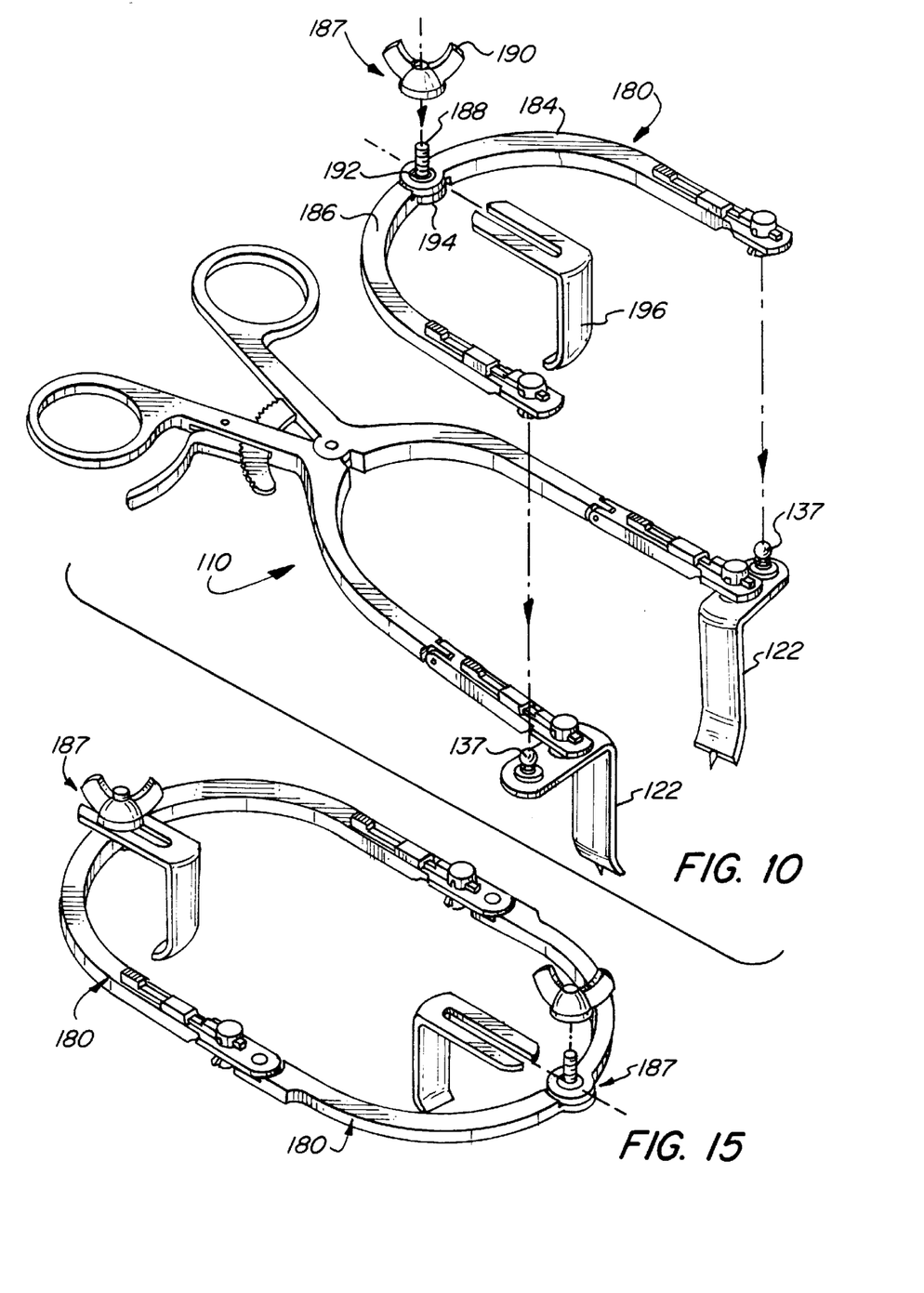
FIG. 10 is top plan view of another embodiment of a spinal tissue retractor in accordance with the invention, which includes a supplemental blade positioned for tissue retraction perpendicular to the main retractor blades.
FIG. 15 is a perspective view of a retractor attachment to a spinal tissue retractor in accordance with FIG. 10, in which two supplemental blades are provided at two perpendicular locations the positioned for tissue retraction perpendicular to the main retractor blades.
Figure 11:
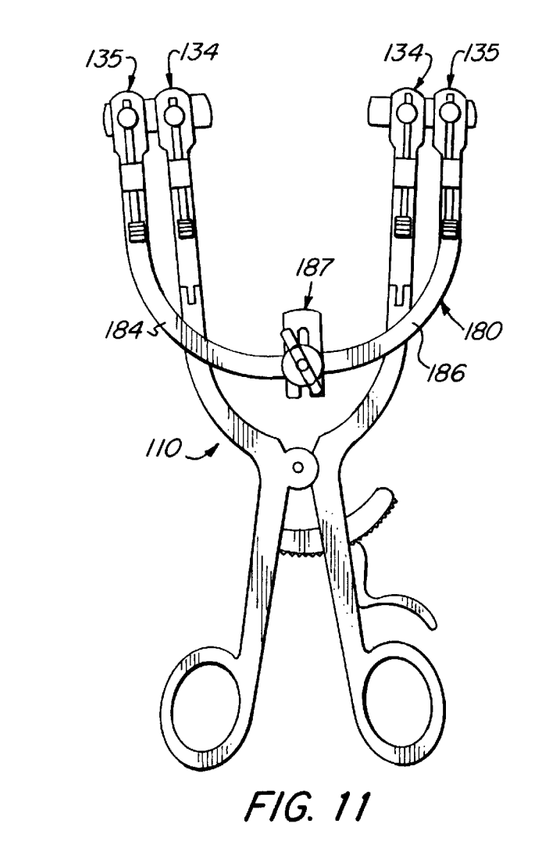
FIG. 11 is top plan view of the retractor of FIG. 10, showing the retractor in the neutral position.
Figure 12:
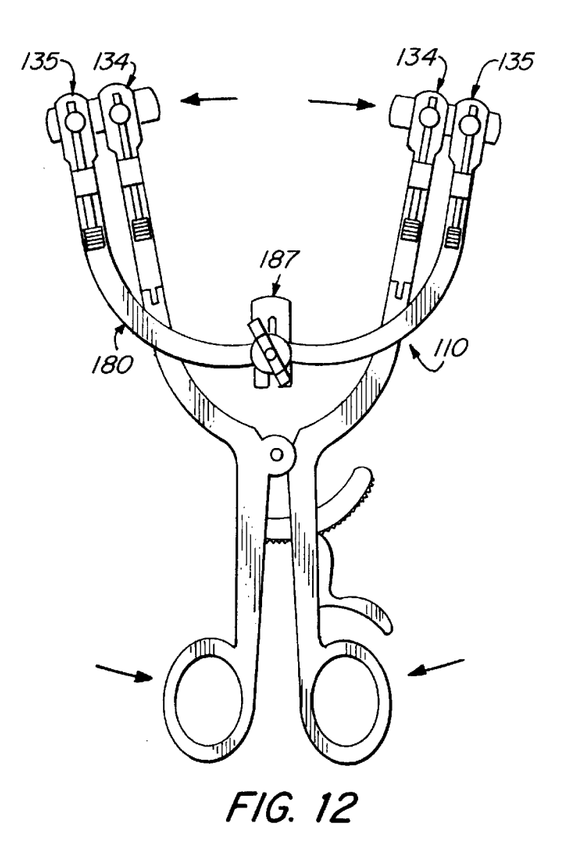
FIG. 12 is top plan view of the retractor of FIG. 10, showing the retractor in the actuated position for tissue retraction.
Figure 13:
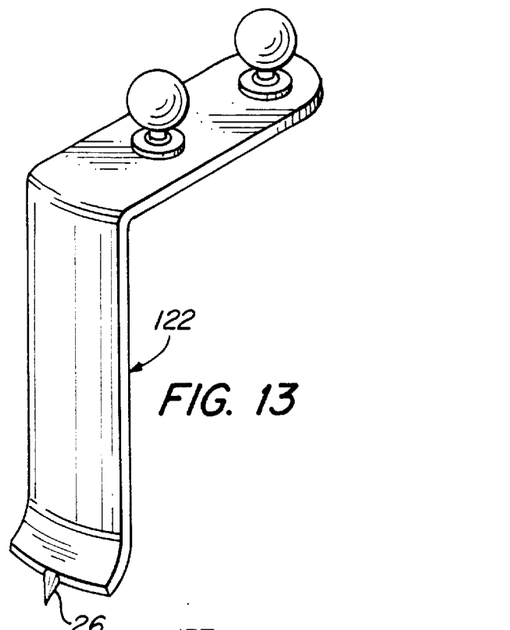
FIG. 13 is a perspective view of a blade of the spinal tissue retractor of FIG. 10.

One or more supplemental retractor blades may also be provided with the retractor 10 at a position or positions to provide a retraction action generally perpendicularly to a retraction action provided by the blades 22. Embodiments of the invention adapted to such supplemental retraction are shown in FIGS. 10–15. In these embodiments, the retractor 110 is essentially as described above, except that blades 122 have two balls for use in ball and socket joints instead of a single ball. As can be seen, blades 122 have a first ball 136 and a second ball 137. The first balls 136 serve as part of the ball and socket connection 134 to the arms 112, 114 of the retractor 110. The second balls 137 serve as part of a ball and socket connection 135 to a linking armature 180. Linking armature 180 has sockets 182 (as described above for mounting blades 22 to the retractor 10) for mounting the linking armature 180 to the blades 122. The linking armature 180 comprises two arms 184 and 186 which are linked by a pivoting/locking fitting 187 such as the bolt 188 with butterfly nut 190 shown as extending through openings 192, 194 in the ends of the two arms 184 and 186. A supplemental retractor blade 196 is preferably secured with the pivoting/locking fitting 187. The supplemental retractor blade 196 is positioned to provide a retraction action generally perpendicularly to a retraction action provided by the blades. As shown in FIG. 15, two such supplemental retractor blades may be provided by use of two linking armatures 180.

In the present invention, the materials used should be suitable materials for surgical use such as stainless steel or titanium.

Figures 18, 19:
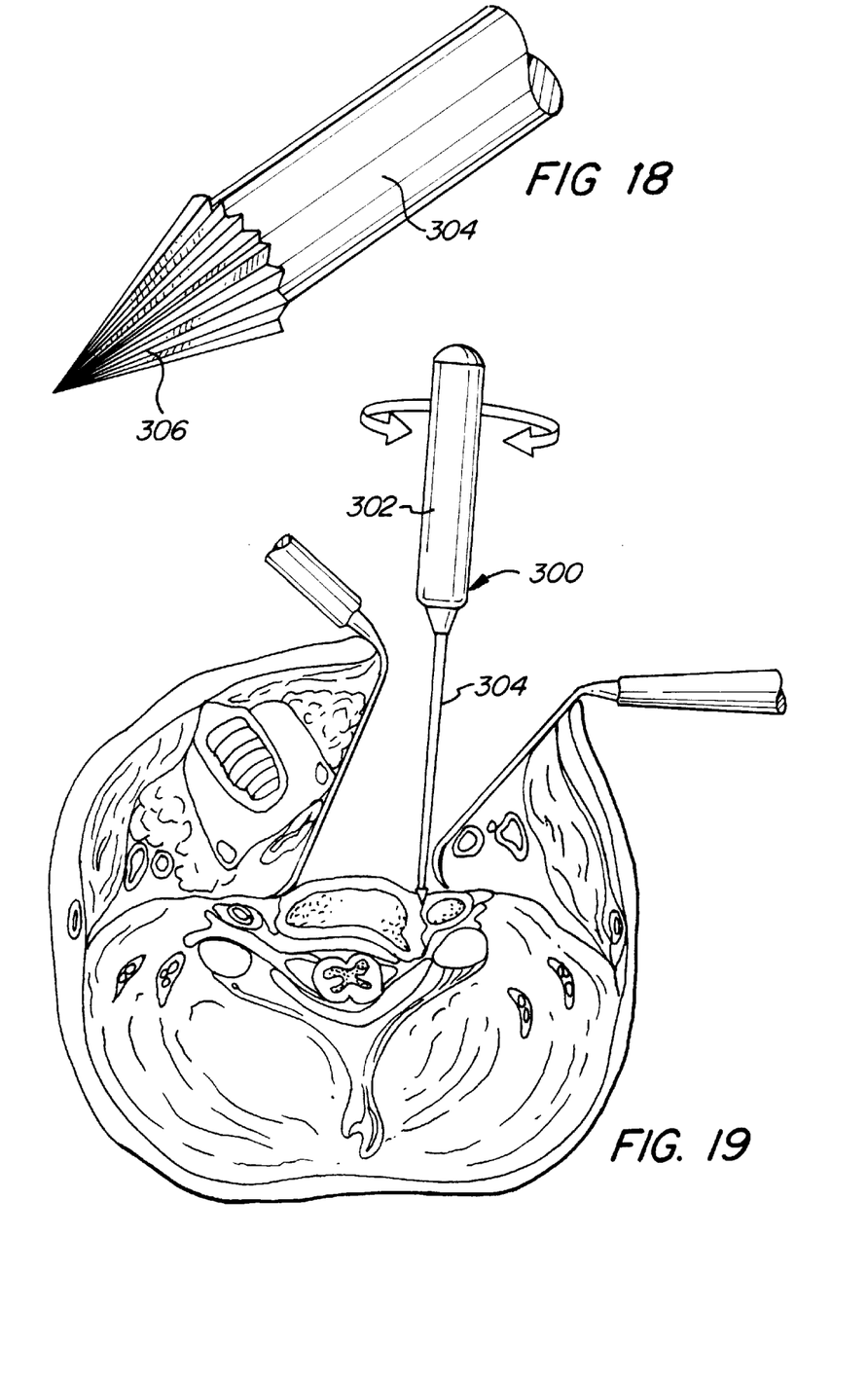
FIG. 18 is a perspective view of an end of a drill tool usable to form a pilot hole in the vertebrae before anchoring the piercing tip of the blade of the spinal tissue retractor.
FIG. 19 is a elevation view showing the use of a drill tool to form a pilot hole in the vertebrae before anchoring the piercing tip of the blade of the spinal tissue retractor.

The present invention improves over prior art retractors in that it uses a different, and more secure method of displacing and holding tissues. In conventional retractors, the blades simply displace the tissue upon actuation of the retractor, but do not anchor it in any way. The effectiveness of the retraction is lost over time as the body tissues move or as a result of jostling of the instrument. In contrast, the present invention relies on pivoting movement of the blades around an anchoring point to displace tissues, thereby providing a more secure retraction, with less effort. A method of the invention, as illustrated in FIGS. 7–9, involves placing the retractor 10 in a wound opening, then securing the piercing tips 26 to a portion of the spine or other bone at positions a distance apart from each other to define a desired surgical field (see FIG. 7). In one embodiment of the method, a pilot hole may be formed in the spine or bone using a drill tool, as illustrated in FIGS. 18 and 19, prior to securing the piercing tips 26 into the bone. As can be seen in FIGS. 18–19, a drill tool 300 comprises a handle 302, a shaft 304, and a drill tip 306. Access to the spine may be obtained by separating the tissues sufficiently, as shown in FIG. 19, then the drill tool 300 is placed in the correct position and rotated to form a small pilot hole. The piercing tips 26 of the retractor 10 are then positioned into and tapped into place to secure them in place in the spine.

The retractor 10 is then operated, as shown in FIG. 8, to cause the blades 22 to separate and to retract tissues surrounding the wound opening by outward pivoting of the blades 22 relative to the position of the piercing tips 26. It is to be appreciated that for the retractor to work in this way, the blades 22 should not be fixed in position relative to the arms 12, 14, otherwise the blades would be prevented from pivoting movement as described. Thus the present invention employs the described swivel mountings to connect the blades 22 to the arms 12, 14. The retractor is then locked in place to position the arms 12, 14 in a fixed position relative to each other. The result is as shown in FIG. 8, where a desired surgical field 200 is available for surgical procedures, and a larger wound opening 202 above the surgical field is available to allow additional room for surgical instruments to be used.

Removal of the retractor 10 after completion of the surgery is the reverse operation, in which the retractor is unlocked, then pulled free of the bone when the tension of the tissues on the blades 22 are released.

It is to be appreciated that the foregoing is illustrative and not limiting of the invention, and that various changes and modifications to the preferred embodiments described above will be apparent to those skilled in the art. Such changes and modifications can be made without departing from the spirit and scope of the present invention, and it is therefore intended that such changes and modifications be covered by the following claims.

What is claimed is:

1. A tissue retractor, comprising:
   a pair of arms, each having a finger grip section, and a pivotal connection between said pair of arms;
   a blade mounted to each of said arms in a position remote from said finger grip sections and said pivotal connection, each said blade having a tip provided with at least one anchoring end for anchoring to bone matter;
   each said blade being mounted to a said arm with a swivel mounting.

2. A tissue retractor in accordance with claim 1, wherein at least one said swivel mounting is capable of pivoting movement in at least a single plane.

3. A tissue retractor in accordance with claim 1, wherein at least one said swivel mounting is capable of pivoting movement in multiple directions.

4. A tissue retractor in accordance with claim 3, wherein said swivel mounting comprises a ball and socket joint.

5. A tissue retractor in accordance with claim 4, herein a ball of said ball and socket joint is provided with said blade, and a socket of said ball and socket joint is provided with said arm.

6. A tissue retractor in accordance with claim 5, wherein said ball is detachable from said socket.

7. A tissue retractor in accordance with claim 6, wherein said socket is split into portions and axially movable in a receiving pocket in said arm of said tissue retractor, whereby said socket may be moved out of said receiving pocket so said portions can be separated to permit removal and insertion of said ball, and whereby said socket may be moved into said receiving pocket to draw said portions together to secure said ball in said socket.

8. A tissue retractor in accordance with claim 7, wherein said socket is axially movable by a sliding cam element fitted into a slot in an upper end of said socket.

9. A tissue retractor in accordance with claim 8, wherein said cam element is finger operable.

10. A tissue retractor in accordance with claim 5, wherein said blades are each provided with first and second balls, and further comprising a linking armature having sockets for receiving said second balls of said blades, to form ball and socket joints, said linking armature having a supplemental retractor blade mounted thereto in a position to provide a retraction action generally perpendicularly to a retraction action provided by said blades.

11. A tissue retractor in accordance with claim 1, wherein said tip anchoring end may be secured to a human spinal vertebrae.

12. A tissue retractor in accordance with claim 1, wherein said tip anchoring end comprises at least one piercing tip.

13. A tissue retractor in accordance with claim 12, further comprising a laterally extending shelf at a lower end of each of said blades.

14. A tissue retractor in accordance with claim 1, further comprising means for locking said arms in fixed relationship.

15. A tissue retractor in accordance with claim 1, further comprising hinges provided in said arms.

16. A tissue retractor in accordance with claim 1, further comprising a supplemental retractor blade provided at a position to provide a retraction action generally perpendicularly to a retraction action provided by said blades.

17. A tissue retractor, comprising:
    a pair of arms, each having a finger grip section, and a pivotal connection between the pair of arms;
    a blade mounted to each of said arms in a position remote from said finger grip sections and said pivotal connection, each said blade having a piercing tip; each said blade being mounted to a said arm with a non-lockable swivel mounting capable of pivoting movement in multiple directions.

18. A tissue retractor in accordance with claim 17, wherein said swivel mounting comprises a ball and socket joint.

19. A tissue retractor in accordance with claim 18, wherein said ball is provided with said blade, and said socket is provided with said arm.

20. A tissue retractor in accordance with claim 19, wherein said ball is detachable from said socket.

21. A tissue retractor in accordance with claim 20, wherein said socket is split and axially movable in a receiving pocket in said arm of said tissue retractor, said socket being axially movable by a finger operable sliding cam element fitted into a slot in an upper end of said socket, whereby said socket may be lowered to permit removal and insertion of said ball, and lifted to secure said ball in said socket.

22. A tissue retractor in accordance with claim 18, further comprising means for locking said arms in fixed relationship.

23. A tissue retractor in accordance with claim 18, further comprising hinges provided in said arms.

24. A tissue retractor in accordance with claim 18, further comprising a supplemental retractor blade provided at a position to provide a retraction action generally perpendicularly to a retraction action provided by said blades.

25. A tissue retractor in accordance with claim 24, wherein said blades are each provided with first and second balls, and further comprising a linking armature having sockets for receiving said second balls of said blades, to form ball and socket joints, said linking armature having a supplemental retractor blade mounted thereto in a position to provide a retraction action generally perpendicularly to a retraction action provided by said blades.

26. A tissue retractor in accordance with claim 17, further comprising a laterally extending shelf at a lower end of each of said blades.

27. A method of retraction of tissues adjacent a bone, using a tissue retractor having a pair of arms, each having a finger grip section, and a pivotal connection between the pair of arms, a blade mounted to each of said arms in a position remote from said finger grip sections and said pivotal connection, each said blade having a tip provided with at least one anchoring end; and a swivel mounting between each said blade and a said arm, comprising:
    placing said blades in a wound opening;
    securing said anchoring ends to a portion of said bone at positions a distance apart from each other to define a desired surgical field;
    operating said retractor to cause said blades to separate and to retract tissues surrounding said wound opening by outward pivoting of said blades relative to the position of said anchoring ends.

28. A method in accordance with claim 27, further comprising the step of locking said retractor arms in a fixed position relative to each other.

29. A method in accordance with claim 28, wherein said step of securing said anchoring ends to a portion of said bone comprises piercing said bone with pointed ends of said blade tips.

\* \* \* \* \*